(12) United States Patent
Kingsley

(10) Patent No.: US 12,275,022 B2
(45) Date of Patent: Apr. 15, 2025

(54) SYSTEMS AND METHODS FOR SIMULATING COUGHS AND SNEEZES

(71) Applicant: DMA International, Inc., Moab, UT (US)

(72) Inventor: Joe D. Kingsley, Moab, UT (US)

(73) Assignee: DMA International, Inc., Moab, UT (US)

( * ) Notice: Subject to any disclaimer, the term of this patent is extended or adjusted under 35 U.S.C. 154(b) by 719 days.

(21) Appl. No.: 17/683,265

(22) Filed: Feb. 28, 2022

(65) Prior Publication Data

US 2022/0186283 A1 Jun. 16, 2022

Related U.S. Application Data

(63) Continuation of application No. 15/627,168, filed on Jun. 19, 2017, now abandoned.

(51) Int. Cl.
| | |
|---|---|
| *B05B 1/12* | (2006.01) |
| *B05B 9/04* | (2006.01) |
| *B05B 9/08* | (2006.01) |
| *C12Q 1/04* | (2006.01) |
| *C12Q 1/22* | (2006.01) |
| *A47L 11/40* | (2006.01) |

(52) U.S. Cl.
CPC .................. *B05B 1/12* (2013.01); *B05B 9/04* (2013.01); *B05B 9/0822* (2013.01); *C12Q 1/04* (2013.01); *A47L 11/408* (2013.01); *C12Q 1/22* (2013.01)

(58) Field of Classification Search
CPC ............ A45D 2200/057; A47L 11/408; C12Q 1/02–08; C12Q 1/22
See application file for complete search history.

(56) References Cited

U.S. PATENT DOCUMENTS

| | | | |
|---|---|---|---|
| 3,955,720 A | 5/1976 | Malone | |
| 4,116,918 A | 9/1978 | Gattner et al. | |
| 5,749,502 A | 5/1998 | Hinds | |
| 5,772,786 A | 6/1998 | De Smet et al. | |

(Continued)

FOREIGN PATENT DOCUMENTS

| | | | | |
|---|---|---|---|---|
| CN | 104497630 A | 4/2015 | | |
| KR | 101211672 B1 * | 12/2012 | ............... | A61B 5/00 |

*Primary Examiner* — Sean E Conley
*Assistant Examiner* — Eric Talbert
(74) *Attorney, Agent, or Firm* — David B. Tingey; K. Russell Griggs; Kirton McConkie

(57) ABSTRACT

The present invention relates to pathogen cleaning and simulation of pathogen spreading. More particularly, some implementations of the described invention relate to systems and methods for spraying materials in a manner that mimics the spreading of pathogens from coughing or sneezing. Some implementations further relate to using a non-aerosol sprayer that produces both a mist and droplets of a mixture containing water, a fluorescent marker, a surfactant, and an antifoaming agent. In some cases, the pump sprayer defines an internal compartment that includes the mixture. In some cases, the sprayer further includes a pump mechanism that is configured to be pumped to compress a gas within the compartment and a release valve that is configured to release pressure within the compartment through a spray nozzle of the sprayer such that droplets and mist of the mixture are sprayed from the nozzle. Other implementations are also described.

20 Claims, 1 Drawing Sheet

(56) References Cited

U.S. PATENT DOCUMENTS

| | | | |
|---|---|---|---|
| 6,524,390 B1 * | 2/2003 | Jones | C09K 11/06 |
| | | | 134/1 |
| 7,718,395 B2 * | 5/2010 | Carling | A61L 2/18 |
| | | | 435/252.4 |
| 8,377,186 B1 * | 2/2013 | Coello | C09D 5/008 |
| | | | 106/31.04 |
| 2012/0175528 A1 * | 7/2012 | Haubrich | H04N 5/33 |
| | | | 252/301.4 R |
| 2017/0226691 A1 | 8/2017 | Farmer et al. | |
| 2018/0363023 A1 | 12/2018 | Kingsley | |

* cited by examiner

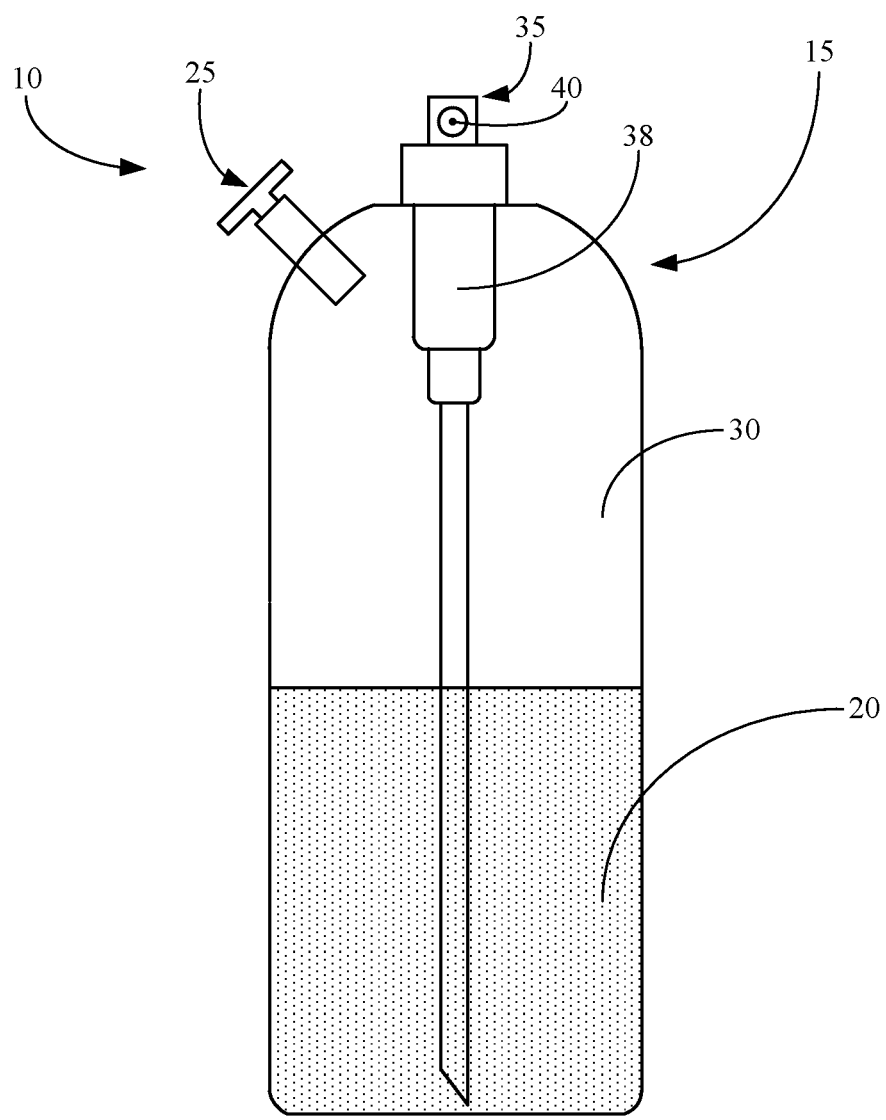

SYSTEMS AND METHODS FOR SIMULATING COUGHS AND SNEEZES

CROSS-REFERENCE TO RELATED APPLICATION

This is a continuation of U.S. Utility patent application Ser. No. 15/627,168, filed Jun. 19, 2017 and entitled SYSTEMS AND METHODS FOR SIMULATING COUGHS AND SNEEZES; the entire disclosure of which is incorporated herein by reference.

FIELD OF THE INVENTION

The present invention relates to the spreading of pathogens and other materials. More particularly, some implementations of the described invention relate to systems and methods for spraying materials in a manner that mimics pathogen spreading through coughing or sneezing. Some implementations further relate to systems and methods for using a non-aerosol, manually-pressurized sprayer that is configured to simultaneously spray both a mist and droplets of a mixture containing a detectable marker (such as a fluorescent marker).

BACKGROUND AND RELATED ART

Many diseases are transmitted through the air. Indeed, several types of viruses, bacteria, fungi, and other pathogens are regularly distributed through the raising of dust, coughing, sneezing, spraying of liquids, and/or through a variety of other similar manners that introduce pathogens into the air. Indeed, in some cases, when a person (or animal) coughs or sneezes, a mist and droplets of saliva and mucus that contain pathogens can diffuse around, and ultimately settle, in the vicinity of the origin of such coughs or sneezes. While such materials can be airborne for some period of time (thereby allowing others to breathe them in), in many cases such materials ultimately settle on surfaces of objects in the vicinity of the coughs or sneezes. Thus, as a person or object touches a surface that has been contaminated with pathogens from coughing or sneezing, such pathogens can readily be passed to, and infect, that person. As a result, some airborne diseases are readily passed from one person to one or more others.

In an effort to reduce the chance of allowing pathogens passed by coughing or sneezing to spread, many have tried to use water, bleach, ammonia, alcohol, antibacterial agents, and/or a wide variety of other cleaning and disinfecting materials to wash surfaces that may be covered with pathogens that were distributed by coughing, sneezing, or a similar method of pathogen distribution. While many such cleaners can be effective at killing or otherwise reducing the amount of pathogens on a surface, many cleaning techniques that use such cleaners are not without their shortcomings. Accordingly, in some cases, it can be relatively easy to not kill or otherwise remove all pathogens from a desired location with such cleaners.

Thus, while systems and methods currently exist that are used to clean up after coughs and sneezes, challenges still exist, including those listed above. Accordingly, it would be an improvement in the art to augment or even replace current techniques with other techniques.

SUMMARY OF THE INVENTION

The present invention relates to the spreading of pathogens and other materials. More particularly, some implementations of the described invention relate to systems and methods for spraying materials in a manner that mimics the spreading of pathogens through coughing or sneezing. Some implementations further relate to using a non-aerosol, manually-pressurized pump sprayer that is configured to produce both a mist and droplets of a mixture containing water, a marker (e.g., a fluorescent marker), a surfactant, and/or an anti-foaming agent.

Some implementations of the described pump sprayer define an internal compartment that includes the mixture. In some cases, the sprayer further includes a pump mechanism that is configured to be pumped to compress one or more gases within the compartment. In some such cases, the sprayer further comprises a release valve that is configured to release pressure within the compartment through a spray nozzle of the sprayer such that droplets and/or a mist of the mixture are sprayed from the nozzle. In some instances, after the mixture has been sprayed, an ultraviolet light (or any other suitable light source in which the marker is readily visible) is used to determine where the droplets and/or mist have settled and/or are otherwise disposed. Additionally, in some cases, after the mixture is sprayed, the area that was sprayed is cleaned (e.g., in normal lighting in which the marker is not readily visible). In some such cases, an ultraviolet light is then used to determine the quality of the cleaning job, by determining how much of the marker is left and visible under the ultraviolet light in the area that was cleaned.

While the methods and processes of the present invention may be particularly useful for mimicking pathogen spreading caused by coughing and/or sneezing, those skilled in the art will appreciate that the described systems and methods can be used in a variety of different applications and in a variety of different areas of manufacture. For instance, instead of being used to mimic coughing or sneezing, some implementations of the described systems and methods are configured to be used to simulate gleeking; expectorating; wheezing; spitting; the expulsion of air from a person's lungs; spittle that projects from a person's mouth during the blowing of air (e.g., to blow out candles on a birthday cake, etc.), speaking, yelling, heaving breathing, etc.; gum splatter; vomiting; and/or any other action in which a mist and/or droplets of a fluid are sprayed and/or are otherwise propelled from one or more points of origin.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWING

In order that the manner in which the above-recited and other features and advantages of the present invention are obtained, a more particular description of the invention will be rendered by reference to specific embodiments thereof, which are illustrated in the appended drawing. Understanding that the drawing is not necessarily drawn to scale or in proper proportion, and that the drawing depicts only a typical embodiment of the present invention and is not, therefore, to be considered as limiting the scope of the invention, the present invention will be described and explained with additional specificity and detail through the use of the accompanying drawing in which:

FIG. 1 illustrates a schematic view of a non-aerosol, manually-pressurized pump sprayer that is configured to produce a mist and/or droplets of a mixture containing a marker, in accordance with a representative embodiment of the invention.

DETAILED DESCRIPTION OF THE INVENTION

The present invention relates to the spreading of pathogens and other materials. More particularly, some embodiments of the described invention relate to systems and methods for spraying materials in a manner that mimics the spreading of pathogens through coughing or sneezing. Some embodiments further relate to using a non-aerosol, manually-pressurized pump sprayer that is configured to produce both a mist and droplets of a mixture containing water, a marker (e.g., a fluorescent marker), a surfactant, and/or an anti-foaming agent. In this regard, some embodiments of the pump sprayer define an internal compartment that includes the mixture. In some cases, the sprayer further includes a pump mechanism that is configured to be pumped to compress one or more gases within the compartment. In some cases, the sprayer further comprises a release valve that is configured to release pressure within the compartment through a spray nozzle of the sprayer such that droplets and/or mist of the mixture are sprayed from the nozzle.

As used herein, the term aerosol, aerosol sprayer, and variations thereof may refer to a non-refillable spray can that includes a pressurized propellant and a payload, and that, in some cases, is configured to only release the payload as a fine mist of liquid particles.

While the described systems can comprise any suitable component, FIG. 1 shows that, in accordance with some representative embodiments, the described system 10 comprises one or more sprayers 15 and/or marker-containing mixtures 20.

With respect to the sprayer 15, the sprayer can comprise any suitable sprayer that is configured to spray the mixture 20 (e.g., so as to simulate a sneeze and/or cough). Some non-limiting examples of such sprayers include an aerosol sprayer, an atomizer, a sprayer having a positive displacement pump, a sprayer having a negative displacement pump, a pressurized container, a nasal-spray bottle, a sprayer comprising a piezoelectric pump, a sprayer comprising a manual pump that is configured to suck fluid (e.g., up a siphon tube) when the pump is actuated, a sprayer comprising a motorized pump, a spray bottle with a trigger-style actuator, a sprayer comprising a pump that is configured to selectively increase a pressure within the sprayer such that the mixture in the sprayer is forced out of a spray nozzle when a valve is opened, and/or any other suitable sprayer.

In accordance with some embodiments, however, the sprayer 15 comprises a non-aerosol sprayer, or a sprayer that is refillable, that can use ambient air to pressurize contents of the sprayer, and/or that is capable of producing a spray that is not a pure aerosol (e.g., that does not consist solely of a colloid of fine liquid droplets in the air). While such a sprayer can comprise any suitable component or characteristic that allows it to function as described herein, in some embodiments, such a sprayer includes a pumping mechanism that is configured to be actuated (e.g., manually, mechanically, electrically, and/or in any other suitable manner) to increase a pressure within the sprayer so as to force the mixture 20 out of the sprayer when a valve is opened. In this regard, FIG. 1 illustrates an embodiment of such a sprayer 15.

Specifically, FIG. 1 shows an embodiment in which the sprayer 15 comprises a manual pump 25 that is configured to be actuated to increase a pressure within an internal compartment 30 of the sprayer. In this regard, the sprayer can comprise any suitable manual pump, including, without limitation, one or more piston pumps, diaphragm pumps, positive-displacement pumps, negative-displacement pumps, fixed-displacement piston pumps, axial piston pumps, radial piston pumps, reciprocating pumps, plunger pumps, centrifugal pumps, roots blowers, rotary pumps, pumps that are actuated by a collar that extends around a nozzle of the sprayer and that are configured to be repeatedly depressed (by the collar) to increase pressure within the compartment, and/or other suitable pump that is configured to allow the sprayer to function as described herein. By way of non-limiting illustration, FIG. 1 shows an embodiment in which the pump 25 comprises a piston pump that is configured to be manually reciprocated to increase pressure within the internal compartment 30 (e.g., so as to force the mixture 20 out of the sprayer when a valve is opened).

With respect to the nozzle, the sprayer 15 can comprise any suitable nozzle that allows it to spray the mixture 20 from the sprayer (e.g., to simulate fluid dispersal from a cough, sneeze, talking, and/or similar action). Some examples of suitable nozzles include, but are not limited to, one or more spray nozzles; depression-engaged nozzles; atomizer nozzles; nebulizer nozzles; nozzles comprising one or more orifices, conical orifices, plain orifices, shaped orifices, and/or other suitable orifices; ultrasonic nozzles; aspirator nozzles; surface-impingement, single-fluid nozzles; pressure-swirl, single-fluid spray nozzles; solid-conde, single-fluid nozzles; compound nozzles; two-fluid nozzles; internal-mix, two-fluid nozzles; rotary atomizers; ultrasonic atomizers; electrostatic atomizers; shaped-orifice nozzles that use a hemispherical shaped (or other suitably shaped) inlet and a V-shaped (and/or other suitably shaped) outlet to cause the flow of the mixture from the nozzle to spread out across the access of the axis of the V notch; hollow-cone nozzles; full-cone nozzles; flat-spray nozzles; solid-stream nozzles; multi-plume spray nozzles; and/or any other suitable nozzles that are capable of spraying the mixture 20 as described herein.

In some embodiments, however, the nozzle 35 comprises a solid-cone nozzle (and/or any other suitable nozzle) that is configured to spray the mixture 20 so that droplets and/or mist of the mixture are projected from the sprayer 15. By way of non-limiting illustration, FIG. 1 shows an embodiment in which the nozzle 35 comprises an orifice 40.

With continued reference to the nozzle 35, the nozzle can be actuated in any suitable manner that allows the mixture 20 to be sprayed through the nozzle as a mist, as droplets, as a stream, and/or in any other suitable manner. Indeed, in some embodiments, the nozzle is actuated and as the nozzle is depressed, when a trigger is pulled, when a switch is engaged, and/or in any other suitable manner. By way of non-limiting illustration, FIG. 1 illustrates an embodiment in which the nozzle 35 is configured to be actuated as it is depressed.

With respect to the release valve, the sprayer 15 can comprise any suitable release valve that is configured to be actuated to release the mixture 20 through the nozzle 35. In this regard, some examples of suitable release valves include a depression-engaged release valve, a cock valve, a metered valve, a squeeze valve, an aerosol spray valve, and/or any other suitable valve. Indeed, in some embodiments (as shown in FIG. 1), the release valve comprises a depression-engaged valve 38 that is configured to be opened when the nozzle 35 is depressed.

The sprayer 15 can be configured to spray the mixture 20 any suitable distance from the sprayer's nozzle 35. In some embodiments, the sprayer is configured to spray the mixture more than (or at least up to) 1, 2, 3, 4, 5, 6, 7, 8, 9, 10, 11, 12, 13, 14, or more feet (or any subrange thereof). Indeed, in some embodiments, the sprayer is configured to spray the mixture at least about 5 feet from the nozzle. In some other embodiments, the sprayer is configured to spray the mixture at least about 6 feet. Indeed, still some other embodiments, the sprayer is configured to spray at least some of the mixture between about 5 feet and about 15 feet (e.g., between about 3 and about 10 feet) so as to have a spray pattern that is similar to that of an uncovered sneeze or cough.

The sprayer 15 is able to spray the mixture 20 such that the sprayed droplets and/or mist settle over any suitable area. Indeed, in some embodiments, when the sprayer is held around a height of a person's mouth when the person is standing (e.g., at between about 2 and about 7 feet above the ground, depending on the person's age and size), the sprayer is configured to spray the mixture such that the mixture settles (without any wind) over an area between about 0.5 and about 500 square feet (or any subrange thereof). Indeed, in some embodiments, the sprayer is configured to spray the mixture (when sprayed at a height of between about 4 and about 7 feet and without ambient wind) such that the spray settles over an area between about 5 square feet and about 40 square feet (e.g., between about 8 and about 16 square feet).

The sprayer 15 can produce droplets and/or particles of the mixture 20 of any suitable size that allows the sprayer to function as described herein. In some embodiments, for instance, the sprayer is configured to spray particles of the mixture such that the majority of the particles are between about 0.01 μm and about 300 μm (or any sub-range thereof) in diameter (or width). Indeed, in some embodiments, the sprayer is configured to spray the majority of the mixture at particle sizes of between about 0.4 μm and about 40 μm. In some embodiments, the sprayer is configured to ensure that some of the particles are small enough that they will stay airborne for a significant period of time (e.g., 1, 2, 3, 4, 5, 6, 7, 8, 9, 10, or more minutes). Indeed, in some embodiments, the sprayer, like a sneeze or cough, is configured to project a mist having fluid particles that will be airborne for about 5 minutes or more.

In addition to spraying small particles, in some embodiments, the sprayer 15 is optionally configured to spray droplets (e.g., along with and/or separate from the mixture particles) of any suitable size (e.g., to simulate droplets of saliva and/or mucus that are expelled). Indeed, in some embodiments, in addition to spraying small particles, the sprayer is also configured to spray droplets between about 10 μm and about 8 mm, or any subrange thereof (e.g., about 100 μm±50 μm).

In addition to the aforementioned components, the sprayer 15 can comprise any other suitable component that allows it to function as intended. Indeed, in some embodiments, the sprayer comprises one or more motorized pumps, batteries, lights, ultraviolet lights, indicator lights, fluorescent lights, switching mechanisms, fluid level indicators, fans (e.g., to blow the mist and/or droplets of the mixture that are released from the sprayer), and/or any other suitable component. By way of non-limiting example, some embodiments of the sprayer (not shown) comprise one or more ultraviolet lights, power sources (e.g., batteries), and/or power source connectors (e.g., plugs). Accordingly, in some such embodiments, the sprayer can be used to both spray and to detect the marker.

As another example of suitable component or characteristic of the sprayer 15, in some embodiments, the sprayer can be any suitable size that allows it to function as intended. Indeed, in some embodiments, the sprayer has an internal volume between about 1 cc and about 10,000 cc (or any subrange thereof). In some cases for instance, the sprayer has an internal volume of between about 2 cc and about 20 cc (e.g., between about 4 and about 8 cc).

As still another example of a suitable characteristic, although some embodiments of the sprayer 15 comprise a flexible container, in some other embodiments, the sprayer comprises a material (e.g., one or more metals, alloys, ceramics, plastics, polymers, and/or any other suitable materials) that are configured to keep an internal volume of the sprayer substantially constant as the internal pressure of the sprayer increases and/or decreases with the sprayer's operational pressure range.

Turning now to the mixture 20, the mixture can comprise any suitable ingredient that allows the mixture to be detected (e.g., visually and/or otherwise) after it has been sprayed, after it has settled, while it is airborne, and/or once the mixture is dried. Indeed, in some embodiments, the mixture comprises one or more solvents, markers, surfactants, anti-foaming agents, and/or other suitable ingredients.

With respect to the solvent, some embodiments of the mixture 20 comprise one or more solvents (or liquids that serve as a carrier for other ingredients and/or into which one or more other ingredients in the mixture go into solution). In this regard, the mixture can comprise any suitable solvent, including, without limitation, one or more types of water, alcohol, oil, non-polar solvents, polar solvents, and/or other suitable solvents. In some embodiments, however, the solvent comprises water. In such embodiments, the water can comprise any suitable water that allows the sprayer 15 to function as described herein. In this regard, some non-limiting examples of suitable waters include distilled water, non-distilled water, de-ionized water, potable water, tap water, purified water, and/or any other suitable form of water. In some embodiments, however, the water comprises distilled water.

Where the mixture 20 comprises water, the mixture can comprise any suitable amount of water. Indeed, in some embodiments, water comprises between about 50% and about 99% (or any subrange thereof), by weight, of the mixture. In some embodiments, the mixture comprises between 89% and about 91.5% water, by weight. In still some other embodiments, the mixture comprises about 90.5% water (±0.5%), by weight.

With reference now to the marker, the mixture 20 can comprise any suitable ingredients that allow the mixture to be identified (visually and/or otherwise) once it has been sprayed. Accordingly, in some embodiments, once the mixture is sprayed, a person can identify the location of the sprayed mixture to determine how well a person can clean-up the sprayed mixture, to determine where spittle from a cough or sneeze may settle, and/or for any other suitable purpose). While the marker can comprise any material that is suitable for use in the mixture and the sprayer 15 and that can be visually and/or otherwise detected after being sprayed, some examples of suitable markers include one or more pigments, dyes, fluorescent markers, phosphorescent markers, markers, coloring agents, tints, colorings, tinctures, ultraviolet markers, infrared markers, radioactive markers, and/or other suitable materials that are able to mark (e.g., visually) locations in which droplets and/or mist containing the marker falls, settles, or are otherwise disposed.

In some embodiments, the marker comprises one or more fluorescent markers, or markers that are visible under ultraviolet light. In this regard, although the marker can comprise any suitable fluorescent markers, some examples of suitable fluorescent markers include, but are not limited to, vitamin A; vitamin thiamine; niacin; riboflavin; tonic water; quinine; chlorophyll; fluorite; calcite; gypsum; ruby; talc; opal; agate; quartz; amber; one or more bluing agents, softening agents, fluorescent dyes, and/or other suitable fluorescent chemicals; anthracene and/or stilbene dissolved in benzene and/or toluene; melamine (e.g., 1,3,5-Triazine-2,4,6-triamine, 2,4,6-triamino-s-triazine, cyanurotriamide, cyanurotriamine, cyanuramide, and/or any other suitable form of melamine); and/or any other suitable material. In some embodiments, however, the marker comprises a powderized melamine resin (e.g., a crushed, hammer-milled, and/or otherwise fragmented melamine resin), such as GLO GERM™ powder (white or any other suitable color), produced by Glo Germ Company, of Moab, Utah, USA.

Where the marker comprises one or more powdered melamine resins, the melamine resin particulates can be any suitable size that allows them to be sprayed from the sprayer 15 and then to be detected (e.g., via ultraviolet light or otherwise). In some embodiments, the marker (e.g., melamine) particulates have a width or diameter of less than about 400 μm (or any subrange thereof). Indeed, in some embodiments, the melamine particulates are less than about 180 μm in diameter. In still other embodiments, the melamine particulates are less than about 100 μm in diameter. In still other embodiments, the melamine particulates are between about 2 and about 8 microns (e.g., between about 4 and about 5 microns).

With reference now to the anti-foaming agent, some embodiments of the mixture 20 comprise one or more anti-foaming agents that are configured to minimize and/or counteract foaming that can occur in the mixture (e.g., as the mixture is mixed, sprayed, contacted with air, and/or otherwise handled). Some examples of such anti-foaming agents comprise one or more defoamers, insoluble oils, polydimethylsiloxanes, silicones, silicon-based defoamers, water-based defoamers, EO/PO-based defoamers, alkyl polyacrylates, alcohols, stearates, glycols, fatty alcohols, ethylene-bis-stearamides, hydrophobic silicas, ester waxes, and/or any other suitable defoaming agent or agents that are capable of reducing foaming in the mixture (e.g., foaming caused by the surfactant, mixing, etc.). Indeed, in some embodiments, the anti-foaming agent comprises a non-toxic, non-irritant material, such as a polydimethylsiloxane emulsion.

Where the mixture 20 comprises one or more anti-foaming agents, the mixture can comprise any suitable amount of the anti-foaming agents. Indeed, in some embodiments, the mixture comprises between about 0.001% and about 6% (or any subrange thereof), by weight, of the mixture. In some embodiments, for instance, the mixture comprises between about 0.03% and about 0.08%, by weight, of the mixture. In some other embodiments, the mixture comprises about 0.04% (±0.02%) of the anti-foaming agent, by weight.

With respect to the surfactant, some embodiments of the mixture 20 comprise one or more surfactants. In this regard, the mixture can comprise any suitable surfactant that is able to increase the mixture's ability to keep the marker suspended (and/or in solution) within the mixture. Some non-limiting examples of suitable surfactants include one or more soaps, dish soaps, linear alkylbenzenesulfonates, lignin sulfonates, fatty-alcohol ethoxylates, alkylphenol ethoxylates, sodium-dodecyl sulfates (SDS), cetrimonium bromides (CTAB), octyl thioglucosides, octyl glucosides, dodecyl maltosides, anionic surfactants, ammonium lauryl sulfates, sodium-lauryl sulfates (SLS), alkyl-ether sulfates, sodium-lauryl-ether sulfates (SLES), sodium-myreth sulfates, docusates (dioctyl-sodium sulfosuccinates), perfluorooctanesulfonates (PFOS), perfluorobutanesulfonates, alkyl-aryl-ether phosphates, alkyl-ether phosphates, alkyl-carboxylates, sodium stearates, sodium-lauroyl sarcosinates, carboxylate-based surfactants, fluorosurfactants, perfluorononanoates (PFOA), perfluorooctanoates (PFO), and/or other suitable surfactants that are capable of improving the mixture's ability to keep the marker suspended within the mixture after the mixture has been mixed. Indeed, in some embodiments, the surfactant comprises a biodegradable, non-toxic, and optionally unscented dish soap, such as DAWN™ brand dishwashing liquid, produced by Procter & Gamble of Cincinnati, Ohio, USA.

Where the mixture 20 comprises one or more surfactants (e.g., dish soap), the mixture can comprise any suitable amount of the surfactant. In some embodiments, the mixture comprises between about 0.001% and about 15% surfactant, by weight (or any subrange thereof). Indeed, in some embodiments, the mixture comprises between about 0.007% and about 1%, surfactant, by weight. In still other embodiments, the mixture comprise about 0.01% (±0.005%) surfactant, by weight.

In addition to the aforementioned characteristics, the described mixture 20 can comprise any other suitable component. In this regard, some non-limiting examples of such components include one or more scents, perfumes, essential oils, oils, polymers, alcohols, hydrocarbons, silicas, talcs, propylene glycols, parabens, triclosans, types of steareth-n, ethanoliamines, quaternary-ammonium compounds, benzisothiazolinones, cyclodextrins, sodium hydroxides, vegetable gums, diluents, emulsifiers, glitters, moisturizers, lotions, and/or any other suitable ingredient or ingredients that allows the mixture to function as described herein.

The various portions of the described system 10 can be made in any suitable manner. In this regard, some non-limiting examples of methods for making the described sprayer 15, mixture 20, marker, and/or other components of the system include extruding, molding, shaping, etching, pressing, cutting, drilling, grinding, boring, machining, sanding, smoothing, buffing, polishing, crushing (e.g., the marker), grinding, mixing, stirring, and/or otherwise forming various components of the system.

The described system 10 and its various components can also be used in any suitable manner. Indeed, in some embodiments, an amount of the mixture 20 is added to the sprayer 15, leaving a sufficient amount of room for air within the sprayer. In some cases, the sprayer is then sealed shut (e.g., the lid and/or nozzle 35 is twisted on or is otherwise coupled to a bottle, flask, cylinder, and/or other container portion of the sprayer). In some embodiments, the sprayer is then pumped (e.g., manually or otherwise) until there is a sufficient amount of pressure within the sprayer to allow the pressure to force the mixture from the sprayer when the valve 38 is opened. Indeed, in some embodiments, the sprayer is pumped until it is difficult to continue pumping the sprayer. In some other embodiments, the sprayer is pumped to provide differential spray patterns. For instance, in some embodiments, a higher pressure in the sprayer can provide a spray that closely resembles an "open air" sneeze, while a lower pressure in the sprayer can provide a spray that closely resembles a cough.

In some cases, once the sprayer 15 is pressurized, a user can then spray the mixture 20 (e.g., so as to simulate a cough and/or sneeze). While the user may hold the sprayer 15 at any suitable height, in some non-limiting cases, the user holds the sprayer at about the user's mouth height. Additionally, while the user can spray the sprayer for any suitable amount of time, depending on the pressure within the sprayer, a specific number of coughs and/or sneezes that are being simulated, a specific type of cough or sneeze that is being simulated, and/or any other suitable factor), in some embodiments, however, the user sprays the mixture from the sprayer for a period of time between about 0.01 seconds and about 10 seconds (or any subrange thereof) for each sneeze and/or cough that is being simulated. Indeed, in some embodiments, the user sprays the mixture for between about 0.5 seconds and about 1.5 seconds for every cough and/or sneeze that is being simulated (e.g., for about 1 second ±0.2 seconds).

In some cases, once the mixture 20 has been sprayed, an individual can attempt to clean an area in which the mixture was sprayed, an individual can attempt to change clothes (e.g., to remove and/or suit up in a hazmat suit or other clothing) that have been sprayed with the mixture, the sprayed mixture is allowed to flow through ventilation ducts, and/or the mixture can be used for any other suitable purpose. Indeed, in some embodiments, after the mixture has been sprayed, a person attempts to clean any surfaces that have been contacted by the mixture. In some cases, the maker is then visualized (or otherwise identified) to determine if the person was able to do a good job in cleaning up (and/or otherwise working with) the mixture, or whether the person missed or otherwise left of some of the marker behind.

Depending on the marker used in the mixture 20, the marker can be detected in any suitable manner that allows a user to determine the marker's location. Indeed, in some embodiments, the marker is visible under one or more ultraviolet lights, black lights, incandescent lights, ambient lights, argon-ion lasers, white lights, and/or other suitable light sources. In some cases, for instance, the marker is readily visible under ultraviolet light. Thus, for instance, after a person has tried to clean up the marker in normal light (e.g., without being able to readily visualize the marker), an ultraviolet light is used to see how well the person did at cleaning up the marker.

In addition to the aforementioned features, the described system 10 can have any other suitable feature. Indeed, in some embodiments in which the sprayer 15 is refillable, the sprayer can shipped empty across the world, without many of the shipping requirements that are laid on aerosol spray bottles.

In another example, some embodiments of the described sprayer 15 are able to spray the mixture 20 without producing undesirable amounts of foam or bubbles, which: can prevent the sprayer from spraying as far as desired, can cause the sprayer to drip and/or to otherwise be messy, and/or can otherwise prevent the sprayer from functioning as intended.

In another example, in some embodiments in which the sprayer 15 can be pumped such that its contents are raised to a desired pressure, the amount of mixture that is propelled from the sprayer and the distance that it is sprayed from the sprayer can be readily modified by changing the sprayer's internal pressure (e.g., to simulate different ways of passing pathogens and/or other materials). In some embodiments, the sprayer can further achieve higher pressures than can be achieved by some other conventional spray bottles (e.g., trigger type spray bottles). Accordingly, in some such embodiments, the described sprayer can spray the mixture further and/or can create smaller particles of the mixture than (e.g., so as to stay airborne longer than would otherwise be achieved by) some conventional spray bottles. Additionally, in some embodiments in which the sprayer is configured to be pumped to increase an internal pressure of the sprayer, the sprayer can be configured to spray relatively thick liquids (e.g., liquids comprising the marker). Moreover, in some such embodiments, the sprayer is configured to spray the mixture as a mist and/or as droplets so as to realistically simulate coughing, sneezing, and/or a similar function.

Thus, as discussed herein, some embodiments of the present invention relate to the spreading of pathogens and other materials. More particularly, some embodiments of the described invention relate to systems and methods for spraying materials in a manner that mimics the spreading of pathogens through coughing or sneezing. Some embodiments further relate to using a non-aerosol, manually-pressurized pump sprayer that is configured to produce both a mist and droplets of a mixture containing water, a marker (e.g., a fluorescent marker), a surfactant, and/or an anti-foaming agent. In this regard, some embodiments of the pump sprayer define an internal compartment that includes the mixture. In some cases, the sprayer further includes a pump mechanism that is configured to be pumped to compress one or more gases within the compartment. In some cases, the sprayer further comprises a release valve that is configured to release pressure within the compartment through a spray nozzle of the sprayer such that droplets and mist of the mixture are sprayed from the nozzle.

The present invention may be embodied in other specific forms without departing from its spirit or essential characteristics. The described embodiments, examples, and illustrations are to be considered in all respects only as illustrative and not restrictive. The scope of the invention is, therefore, indicated by the appended claims rather than by the foregoing description. All changes that come within the meaning and range of equivalency of the claims are to be embraced within their scope. In addition, as the terms on, disposed on, attached to, connected to, coupled to, etc. are used herein, one object (e.g., a material, element, structure, member, etc.) can be on, disposed on, attached to, connected to, or coupled to another object—regardless of whether the one object is directly on, attached, connected, or coupled to the other object, or whether there are one or more intervening objects between the one object and the other object. Also, directions (e.g., front back, on top of, below, above, top, bottom, side, up, down, under, over, upper, lower, lateral, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

What is claimed is:

1. A method for checking cleanliness of a surface, the method comprising:
providing a mister, the mister comprising:

a container with a pump and a nozzle, the container comprising a mixture that comprises:
  a fluorescent, powdered marker having a particulate size that is smaller than about 100 μm to allow a portion of the mixture to remain airborne to replicate a respiratory biological dispersion after the mixture has been sprayed from the nozzle;
  water;
  a surfactant to maintain the fluorescent, powdered marker in suspension within the mixture; and
  an anti-foaming agent; and
spraying the mixture from the nozzle so as to: (i) simultaneously release droplets and a mist comprising the mixture, wherein the droplets have a width between 50 μm and 8 mm and particles of the mist have a width between 0.4 μm and 40 μm, and (ii) allow the mixture to settle on an area of more than 5 square feet of the surface; and shining ultraviolet light on the surface to detect the fluorescent marker on the surface.

2. The method of claim 1, wherein the fluorescent, powdered marker comprises melamine powder having a particle size that is less than 100 μm to allow the portion of the mixture to remain airborne to replicate the respiratory biological dispersion after the mixture has been sprayed from the nozzle.

3. The method of claim 1, wherein the fluorescent, powdered marker, once sprayed from the mister, is not readily visible under normal lighting conditions, but is readily visible under ultraviolet light.

4. The method of claim 3, further comprising:
  cleaning the surface to remove at least a portion of the fluorescent, powdered marker from the surface; and
  shining ultraviolet light on the surface to detect an efficacy of the cleaning of the surface.

5. The method of claim 1, wherein the fluorescent, powdered marker in the mixture has a particle size that is less than about 8 μm in width.

6. The method of claim 3, wherein the cleaning is done under the normal lighting conditions in which the fluorescent, powdered marker is not readily visible.

7. The method of claim 1, further comprising manually pumping the pump to increase pressure within the container such that when the mixture is sprayed from the nozzle, the nozzle simultaneously releases the droplets and the mist, with the droplets having their width between 50 μm and 200 μm and the particles of the mist having their width between 0.4 μm and 30 μm.

8. The method of claim 1, wherein the fluorescent, powdered marker has a width between about 2 microns and about 8 microns to allow a portion of the mist that comprises the fluorescent, powdered marker to remain airborne to help replicate the respiratory biological dispersion after the mixture has been sprayed from the nozzle.

9. A method for checking cleanliness of a surface, the method comprising:
  providing a mister, the mister comprising:
    a container with a pump and a fixed-cone nozzle, the container comprising a mixture that comprises:
      a fluorescent, powdered marker having a particulate size that is smaller than about 100 μm to allow a portion of the mixture to remain airborne to replicate a respiratory biological dispersion after the mixture has been sprayed from the fixed-cone nozzle;
      water;
      a surfactant to maintain the fluorescent, powdered marker in suspension within the mixture; and
      an anti-foaming agent;
  placing the mister at a height that is between 2 and 7 feet above the surface and then spraying the mixture from the fixed-cone nozzle so as to: (i) simultaneously release droplets and a mist comprising the mixture, wherein the droplets have a width between 50 μm and 8 mm and particles of the mist have a width between 0.4 μm and 40 μm, and (ii) allow the mixture to settle on the surface over an area of more than 5 square feet;
  cleaning the surface to remove at least a portion of the fluorescent, powdered marker from the surface; and
  shining ultraviolet light on the surface to detect an efficacy of the cleaning of the surface.

10. The method of claim 9, wherein the water accounts for between 70% and about 95%, by weight, of the mixture, and wherein the fluorescent, powdered marker comprises between 3% and 15%, by weight, of the mixture.

11. The method of claim 10, wherein the surfactant comprises between 0.002% and 0.05%, by weight, of the mixture, and wherein the anti-foaming agent comprises between 0.01% and 0.05%, by weight, of the mixture.

12. The method of claim 9, wherein the fluorescent, powdered marker, once sprayed from the mister, is not readily visible under normal lighting conditions, but is readily visible under ultraviolet light, and wherein the cleaning of the surface is accomplished under the normal lighting conditions.

13. The method of claim 9, further comprising pumping the pump to increase pressure within the container to change a dispersal characteristic of the fluorescent, powdered marker from the fixed-cone nozzle.

14. The method of claim 9, wherein the spraying the mixture from the fixed-cone nozzle further includes spraying at least some of the mixture between 5 feet and 15 feet from the mister.

15. A method for checking cleanliness of a surface, the method comprising:
  providing a mister, the mister comprising:
    a container with a pump and a fixed-cone nozzle, the container comprising a mixture that comprises:
      a fluorescent, powdered marker having a particulate size that is smaller than about 100 μm to allow a portion of the mixture to remain airborne to replicate a respiratory biological dispersion after the mixture has been sprayed from the fixed-cone nozzle, wherein the fluorescent, powdered marker, once sprayed from the mister, is not readily visible under normal lighting conditions, but is readily visible under ultraviolet light;
      water;
      a surfactant to maintain the fluorescent, powdered marker in suspension within the mixture; and
      an anti-foaming agent;
  placing the mister at a height that is between 2 and 7 feet above the surface and then spraying the mixture from the fixed-cone nozzle so as to: (i) simultaneously release droplets and a mist comprising the mixture, wherein the droplets have a width between 50 μm and 200 μm and particles of the mist have a width between 0.4 μm and 30 μm, and (ii) allow the mixture to settle on the surface over an area of more than 5 square feet and less than 500 square feet;
  cleaning the surface under the normal lighting conditions to remove at least a portion of the fluorescent, powdered marker from the surface; and
  shining ultraviolet light on the surface to detect an efficacy of the cleaning of the surface.

16. The method of claim 15, wherein the water accounts for between 70% and about 95%, by weight, of the mixture, wherein the fluorescent, powdered marker comprises between 3% and 15%, by weight, of the mixture, wherein the surfactant comprises between 0.002% and 0.05%, by weight, of the mixture, and wherein the anti-foaming agent comprises between 0.01% and 0.05%, by weight, of the mixture.

17. The method of claim 15, wherein the fluorescent, powdered marker has a width between about 2 microns and about 8 microns to allow a portion of the mist that comprises the fluorescent, powdered marker to remain airborne to help replicate the respiratory biological dispersion after the mixture has been sprayed from the fixed-cone nozzle.

18. The method of claim 15, wherein the water accounts for between 70% and about 95%, by weight, of the mixture, wherein the fluorescent, powdered marker comprises between 8.75% and 10.45%, by weight, of the mixture, wherein the surfactant comprises between 0.002% and 0.05%, by weight, of the mixture, and wherein the anti-foaming agent comprises between 0.03% and 0.08%, by weight, of the mixture.

19. The method of claim 15, wherein the fluorescent, powdered marker comprises a powdered melamine resin having a width of less than about 8 μm.

20. The method of claim 18, wherein the anti-foaming agent comprises polydimethylsiloxane.

\* \* \* \* \*